United States Patent [19]

Lin et al.

[11] Patent Number: 5,314,581
[45] Date of Patent: May 24, 1994

[54] APPARATUS FOR SIMULATING PROCESSING PARAMETERS AND PREDICTING VARIABLES IN A PAPERMAKING OPERATION INCLUDING SEQUENTIAL PULSATION, GRAVITY AND VACUUM DRAINAGE, FINES RETENTION AND PAPER FORMATION

[75] Inventors: John T. Lin; Michael A. Schuster; Richard A. Hobirk; Alan J. Schellhamer, all of Jacksonville, Fla.

[73] Assignee: Betz PaperChem, Inc., Jacksonville, Fla.

[21] Appl. No.: 805,266

[22] Filed: Dec. 10, 1991

[51] Int. Cl.⁵ .................... D21C 7/00; G01N 11/00
[52] U.S. Cl. .................... 162/263; 162/351; 73/61.62; 73/61.64; 73/61.67
[58] Field of Search .............. 162/263, 258, 354, 374, 162/335, 274, 198, 351, 352; 73/63, 61.62, 61.64, 61.67

[56] References Cited

U.S. PATENT DOCUMENTS 4,838,996 6/1989 Kallmes .................... 162/374

OTHER PUBLICATIONS

J. E. Unbehend, "Laboratory Drainage Testers-A Critical Review", TAPPI, 1990, pp. 363–375.
K. W. Britt & J. E. Unbehend, "New Methods For Monitoring Retention", TAPPI vol. 59, No. 2, pp. 67–70, Feb. 1976.

Primary Examiner—Steve Alvo
Attorney, Agent, or Firm—Alexander D. Ricci; Gregory M. Hill

[57] ABSTRACT

An apparatus and method to simultaneously evaluate the drainage, retention and formation characteristics of paper pulp comprising mixing the paper pulp furnish in the top chamber of the apparatus, releasing the furnish into a middle chamber via a valve having a cone shaped structure for even distribution of the furnish onto a wire screen, and utilizing a time delay before opening a vent valve in order to attenuate impingement forces. The apparatus utilizes a rotating blade under the wire screen to duplicate the pulsation forces of full scale papermaking equipment, an externally applied means to assist in the removal of water similar to a paper machine couch roll. Data generated during the foregoing steps is fed into a computer to evaluate the entire free water drainage process of the furnish. The device is able to set parameters to simulate the water removal process on most paper machines via level control and duration of pertinent variables.

5 Claims, 9 Drawing Sheets

APPARATUS FOR SIMULATING PROCESSING PARAMETERS AND PREDICTING VARIABLES IN A PAPERMAKING OPERATION INCLUDING SEQUENTIAL PULSATION, GRAVITY AND VACUUM DRAINAGE, FINES RETENTION AND PAPER FORMATION

FIELD OF THE INVENTION

The invention relates to an apparatus designed to separate fibrous material such as paper pulp from the water phase by forming a web or sheet without destroying uniformity of fiber dispersion. Particularly, it relates to a testing apparatus designed to evaluate drainage, retention, and formation of a paper pulp furnish.

BACKGROUND OF THE INVENTION

In a typical paper machine, a pulp furnish consisting of fibers and filler slurry is jetted from a headbox onto a moving paper forming surface, usually a wire. The wire is an endless loop; the top carrying pulp furnish is usually called the forming section. Underneath the forming section are many stationary drainage elements. They assist drainage in different ways depending on their design and position on the machine.

First, the wire travels across a series of hydrofoils (or table rolls in early models of Fourdrinier machine). White water drains from the pulp in response to the gravity and to the pulsation forces generated by these drainage elements. (The drainage in this period is therefore referred to as the pulsation/gravity drainage). Furnish consistency increases gradually and dewatering becomes more difficult as the wire travels farther down the table. Vacuum assisted hydrofoils are used to sustain higher drainage, and then high-vacuum flat boxes are helpful in removing as much water as possible. Finally, a suction couch roll provides suction forces to improve water removal. The sheet then transfers to the pressing and drying sections for residual water removal.

The efficiency of a paper or paperboard making process is determined by many factors. At the wet end, important factors are the drainage rate of the furnish, the retention of fibers or fillers, and the formation. They affect machine runability, the production rate, white water system cleanliness, cost and quality of the product, etc. For instance, poor retention of filler and fines lowers the opacity of the paper. Ineffective single-pass retention of fiber and filler results in a high solid content in the white water system. Accumulation of fines in the headbox retards drainage. When drainage is poor the web may contain too much water to withstand the stress exerted by the press roll; therefore, the machine has to slow down and the production rate suffers. If the drainage is high, the papermakers can either pursue a higher production rate, or they can dilute the headbox furnish to allow for better formation. Formation impacts the strength, the appearance of the paper sheet and many other aspects. All these factors influence machine runability.

Improving drainage, retention, and formation are continual tasks for papermakers. The rate of water removal is often the rate determining step in the total papermaking process. For a given paper machine, the rate of water removal can be changed by changing fiber composition, degree of refining, non-fibrous materials (clay, titanium dioxide, calcium carbonate, etc.), and/or by the addition of wet end chemicals.

A wide range of retention aids, drainage aids, and formation aids are utilized in the paper industry to achieve this goal. To predict on-machine performance, the papermakers usually rely on certain types of testing devices. Unfortunately, a drainage testing device may be misleading if its drainage mechanism is dissimilar from the production machine's drainage. The effect of various drainage mechanisms will be clarified while reviewing conventional devices relevant to this invention.

Testing results obtained from most of the prior art devices are incomplete, because they do not duplicate the paper machine free water removal process. First, these devices are either for gravity or vacuum drainage exclusively. Their testing disregards the sequential drainage process normally found on paper machines, i.e., a pulsation/gravity drainage followed by a vacuum drainage. Secondly, pulsation forces are lacking in those devices. On the other hand, pulsation forces are known to have a major impact on drainage of furnishes on paper machines. Third, conventional devices cannot assess the inter-dependent variables (drainage, retention, and formation) in a single test. Details of those devices and their deficiencies are discussed in the Related Art Section. Therefore, there is a need for a device that approximates the dewatering process existing on a paper machine, is reproducible, and is laboratory-sized.

DESCRIPTION OF RELATED ART

Recently, J. E. Unbehend, in an article entitled "Laboratory Drainage Testers—A Critical Review", TAPPI Proceedings, pp 363–375 1990 Papermakers Conference, reviewed numerous drainage/retention testers including those adopted to establish TAPPI or SCAN standards. For drainage testing, TAPPI documented methods include T 221 om-88 entitled, "Drainage Time of Pulp", and T 227 om-85, "Freeness of pulp". The former is known as the sheet mold drainage time. The latter is well known as Canadian Standard Freeness (CSF).

Another standard drainage device is the Schopper-Riegler wetness tester from SCAN Standard C19:65. All of these drainage testers measure the freeness or drainage time of a stock under static conditions, i.e., essentially no shearing or turbulence during dewatering.

The Canadian Standard Freeness Tester, the most widely used drainage tester, is sometimes misleading. For instance, a newsprint furnish usually has a much lower CSF value (slower drainage) than unbleached kraft. However, the former drains much faster on a production machine than the latter due to grade type and machine speed. The example indicates that the Canadian Standard Freeness Tester cannot be used to compare furnishes of different types. Given the same type of furnish with various treatments, the CSF tester always predicts that drainage is related to flocculation and retention. However, it is known that retention aids may impede drainage on a high speed paper machine (due to increased fiber fines retention). Such discrepancies occur because the drainage mechanism in a Canadian Standard Freeness Tester is fundamentally different from that on the high speed paper machine. The CSF tester responds to flocculation in the absence of shear. It is well known that turbulence generated by hydrofoils and other drainage elements can affect the drainage rate dramatically. Usually, higher machine speed yields greater turbulence. The effect of machine speed on drainage, retention, and formation was reviewed by Marton (J. Marton, TAPPI Proceedings, Papermakers Conference, pp 211-217, 1988 and TAPPI Journal, pp 67-71, April (1988). In fact, it is a common practice for papermakers to adjust the hydrofoil angles and spacing to change the drainage and retention behaviors. Since the CSF tester does not produce turbulence, its testing results can be misleading. The same argument applies to other drainage apparatus that are conducted under basically static conditions.

The Dynamic Drainage Jar, described in "New Methods for Monitoring Retention", TAPPA, 59(2):67(1976), was developed by Britt and Unbehend to study fines retention of a stock sample in a dynamic, turbulent condition generated by an impeller. The device can be used for drainage by measuring the drainage time of a fixed volume of furnish under agitation. Unbehend commented that the Dynamic Drainage Jar provides an excellent way of measuring the retention of fines under dynamic conditions, but the device evaluates the drainage qualitatively rather than quantitatively. There are a few models of drainage devices which are essentially vacuum assisted Dynamic Drainage Jars, including the Vacuum Water Release Analyzer, described in "Water Removal During Sheet Formation", TAPPI 63(4):67 (1980), to measure the dryness of a sheet after exposure to an exactly controlled vacuum, the Dynamic Drainage Analyzer (DDA) to control dosage and stirring time, described in "The Dynamic Drainage Analyzer (DDA)", TAPPI Proceedings, Papermakers Conference, pp 239-245, 1990, and the Drainage, Vacuum and Retention Tester (DVRT) which uses electrodes in measuring drainage time ("A New Technique for Specific Filtration Resistance Measurement", Fluid/Particle Separation Journal, Vol. 2, No. 2, pp 109-114, June, 1989). The G/W Drainage Tester, described in U.S. Pat. No. 4,613,406 uses a constant flow rate vacuum to conduct drainage and uses the vacuum vs. time curve to determine furnish drainage characteristics.

In the Dynamic Drainage Jar or its modifications, stirring with an impeller prevents the stock sample from forming a mat. Therefore, the Dynamic Drainage Jar is supposed to simulate the early stage drainage, in which the turbulence acting on the stock is carried over from the headbox. However, it is a reasonable assumption that the action of pulsation forces created by hydrofoils is different from shearing forces generated by the impeller; simply because the impeller disrupts the entire stock sample, while hydrofoils affect the bottom layers more than the top layers of the furnish. Marton's review article reported that, if the turbulence is too low, sheet sealing effects may take place on a paper machine. Impeller generated turbulence can never reproduce such an effect, because the entire stock sample is disrupted. The purpose behind the Dynamic Drainage Jar is to measure the retention prior to mat formation. This explains why the Dynamic Drainage Jar cannot truly simulate the action of hydrofoils on a paper machine, particularly at the late stage of drainage when the mat is formed or is about to form.

In the G/W Drainage Tester or the vacuum-assisted Dynamic Drainage Jars, the drainage process begins with a vacuum pressure without going through a pulsation/gravity drainage period. In fact, certain furnishes such as newsprint have difficulties in drainage using these devices without the assistance of vacuum pressure. However, such a process does not represent typical paper machines on which the furnish slurries are usually de-watered to about 75-95% of its initial water content before it reaches the first low vacuum box. The "Dynamic Drainage Analyzer (DDA)" article reports that early application of vacuum suction results in fiber mat formation in an early stage, verified by increased retention.

The effect of pulsation forces on retention was first investigated by Britt et al., "Observations on Water Removal in Papermaking", TAPPI Journal, July 1986 pp 76-79. Their device, an early version of the Turbulence Pulse Drainage Apparatus, applied alternating air/vacuum pressure to produce pulsation. Unfortunately, the device is difficult to use. If the air to vacuum ratio is not properly adjusted, a positive pressure may impede the drainage. Experimental data reported using a vacuum pulsation device, described in "A new Vacuum Pulsation Drainage Procedure for Determining Fine Particle Retention" by R. W. Davison, TAPPI Journal, August 1989, which is essentially similar to the Turbulence Pulse Drainage Apparatus, indicate that fines retention decreases as pulsation forces increase. However, it seems that the pulsation drainage time changes erratically. With this type of device, the major negative is the introduction of air into the system. Entrained air has the potential to impede drainage which could lend to erroneous results. For this reason, these devices may be proper for retention studies but are not suitable for drainage testings.

An understanding of the drainage mechanisms can help papermakers use a testing device properly in simulating the on-machine behavior. Drainage takes place through different mechanisms dependent upon the type of furnish, the basis weight of the furnish slurry and on its interactions with the drainage elements. J. P. Casey suggests, in "Pulp and Paper Chemistry and Chemical Technology" (Vol. 2, Wiley-Interscience) p.980, that a distinction exists between the filtration mode and the thickening mode of water removal from a fiber pulp furnish. In filtration, mat formation takes place on the wire surface serving as a filtering medium for the remainder of the original consistency stock.

In contrast, the thickening mechanism can be viewed as being a condition of turbulence so great that the mat cannot form until a large amount of water has been removed. The consistency of the stock above the wire increases uniformly until water removal without mat formation is impossible. For relatively slow speed paper machines, filtration is the predominant, but not the sole drainage mechanism. For relatively fast paper machines, thickening is the predominant mechanism.

From a drainage mechanism point of view, a static drainage tester such as the Canadian Standard Freeness tester may be proper in predicting the drainage of a slow-speed paper machine. However, the type of drainage aid must remain constant for valid testing. High molecular weight polymers cannot be adequately compared to low molecular weight polymers which also have proven benefit as drainage aids. The Dynamic Drainage Jar and its analogs are proper to simulate high speed drainage. However, drainage on most paper machines is a combination of filtration and thickening. The thickening mode may be more predominant than the filtration mode in the front section of the forming table, and the reverse is true in the rear section. A good drainage tester therefore must cover the entire drainage process. It should reveal the effects of pulsation/gravity vs.

vacuum, filtration vs. thickening, or any combination thereof.

Furnish impingement is another factor that can alter drainage, retention and formation characteristics. In the traditional drainage testers mentioned previously, the furnish slurry must be poured onto the wire screen while the bottom of the stock sample vessel must be closed or blocked so that the stock will not drain. The cover or blocking is then removed to start drainage. As a consequence, the furnish does not have an initial Z-directional momentum, i.e., no impingement action. This process is only an extreme style of furnish delivery. On paper machines, particularly the high speed ones, the furnish is often jetted to the wire at a certain angle. White water starts draining immediately due to the directional momentum; this style of delivery is known as pressure forming. Instant drainage may be undesirable because it hurts formation and retention. In this case, the papermakers will use a forming board of few or no openings to attenuate early drainage (velocity forming). Therefore, an ideal drainage tester should be able to adjust and simulate the effect of impingement forces.

Formation is another important variable that papermakers would like to predict whenever they change retention or drainage programs on the wet end. Formation is normally measured based on optical or surface roughness characteristics. The Formation Index usually correlates to the air-flow resistivity (or inverse of the porosity). The better the formation, the higher the resistivity is, due to evenly distributed fibers or fillers resulting in a higher air-flow resistivity. Therefore, by measuring the pressure drop and the flow rate of air, the resistivity of the sheet can be obtained to predict the formation. Test method T 251 cm-85, "Air Permeability of Porous Papers, Fabrics and Pulp Handsheets" measures the air permeability of dried sheet. The vacuum assisted Dynamic Drainage Jar or its modifications can be used to measure the porosity of a wet pad. However, since the drainage mechanism in those devices is dissimilar (i.e., measures compaction and sealing from the start) from papermachine drainage, the porosity of the wet pad as it forms in such a device may be misleading.

Drainage, retention, and formation are inter-dependent variables in a paper making process. It is well known that changing any one of these variables will change the other. Therefore, an ideal drainage tester must be able to evaluate these variables simultaneously in a single test. Unfortunately, none of the relevant conventional devices are capable of doing so.

The drainage mechanisms mentioned above clearly indicate that an ideal drainage tester must cover the entire drainage process in order to evaluate the drainage behavior correctly. Secondly, such a tester must be able to generate adjustable pulsation forces and demonstrate the effect of such on three important variables, namely the drainage, the retention, and the formation. The device must evaluate them altogether in a single test, because these variables are inter-dependent. Also, it must be able to distinquish furnish variation, refining levels, additive treatment. If testing device cannot predict the drainage behavior, the papermakers must only rely on trials which may be time consuming and extremely costly.

SUMMARY OF THE INVENTION

This invention comprises an apparatus and method for predicting the drainage, retention and formation characteristics of a papermaking operation. The turbulent forces of a paper machine are simulated by using a rotating hydrofoil assembly. Drainage assessment covers the entire free water removal region. The pulsation/gravity drainage and the vacuum drainage are conducted and assessed sequentially. The water removal rates as measured on a paper machine with a gamma gauge can be matched by adjusting the hydrofoil speed and vacuum sequence of the drainage device. Formation and consistency of the wet pad as it is formed in the drainage test can be measured simultaneously. Fines retention can be evaluated from gravimetric analysis of white water. The device is able to set variables to simulate the water removal process on most paper machines via level control and duration of the pertinent variables.

The device of this invention, therefore differentiates itself from the known devices previously described by its ability to generate pulsation forces, conduct a complete pulsation/gravity and vacuum drainage simulation, assess the drainage, retention and formation performances simultaneously, and control pertinent variables to mimic most paper machines.

DETAILED DESCRIPTION of THE INVENTION

Figure 1:
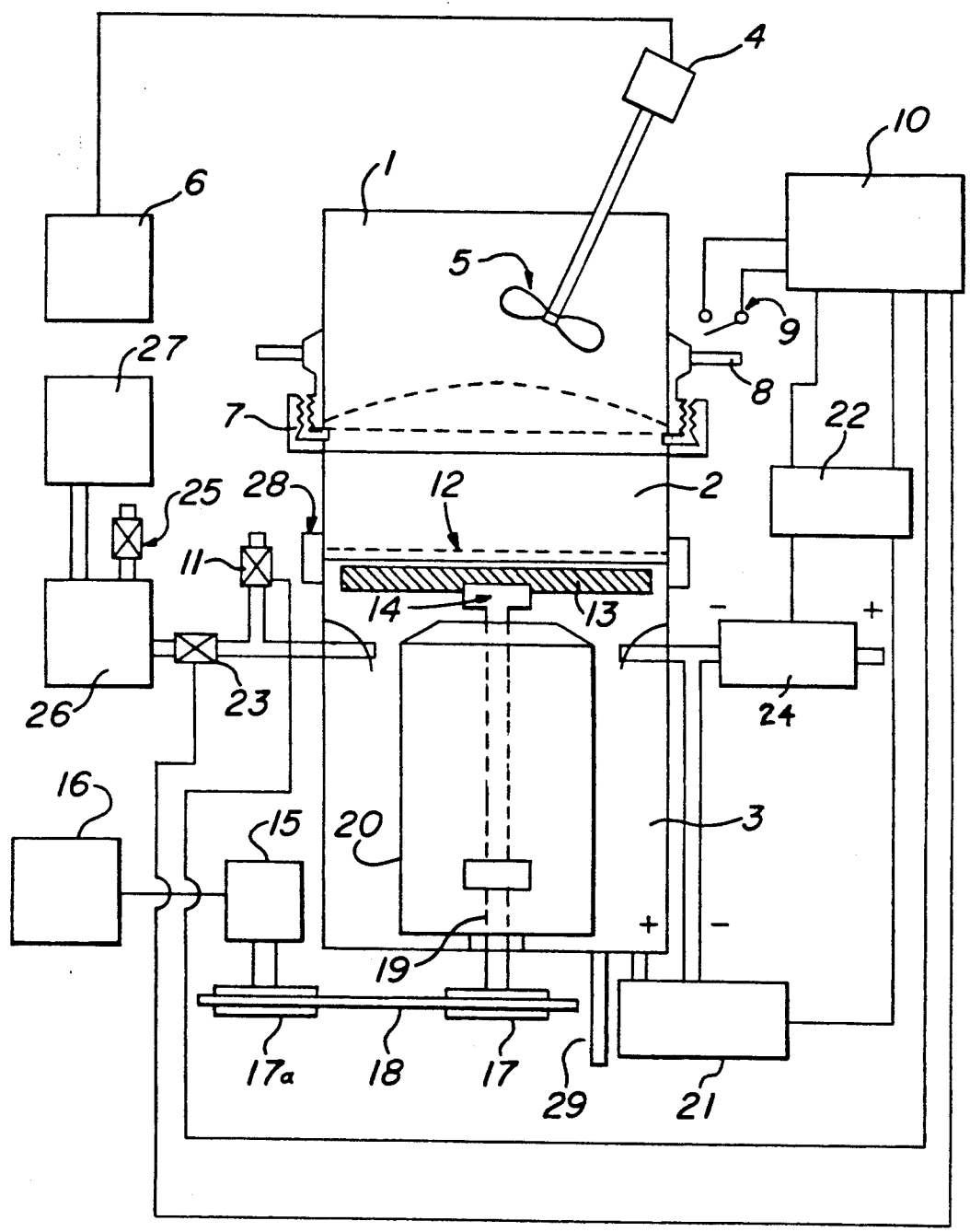
FIG. 1 is a schematic drawing of the apparatus of this invention.

The apparatus of this invention, as shown in FIG. 1, is generally cylindrical in shape and consists of three chambers, first a furnish delivery (upper) chamber 1, above a second, paper sheet forming chamber 2, and a third, white water collection and vacuum (bottom) chamber 3, below the second chamber 2.

Furnish in the upper chamber 1 is stirred by a mixer 4 having a blade 5. The rotational speed of the mixer blade 5 is determined by a controller unit 6. After mixing wet end additives in the upper chamber 1, the furnish is released through a valve 7, referred to as a furnish delivery valve, into the paper sheet forming chamber 2. A handle 8 secured to the outer surface of the valve 7 is manually rotated circumferentially about the outer perimeter of the apparatus to permit the valve 7 to release the furnish into the second chamber. Movement of the handle 8 triggers a micro switch 9. The micro switch 9 signals a computer 10 to activate a furnish impingement control process.

Initially, a vent valve 11 is closed. During the furnish impingement control process, backup pressure, generated internally as the furnish drops, allows furnish to stay momentarily on top of a paper forming surface 12. Longer backup pressure time increasingly reduces or attenuates the impingement force. When a predetermined delay time expires, the vent valve 11 opens. As soon as the vent opens, backup pressure disappears and the paper forming surface facilitates the separation of the fibers from the white water in response to gravity forces, head pressure, and the hydrodynamic turbulence generated by a rotary hydrofoil means located underneath the paper forming surface 12.

The hydrofoil means consists of a blade 13 secured to a holder 14. The hydrofoil's rotation is powered by a mechanical power source, such as a variable speed motor 15 and is adjusted by a controller unit 16. The mechanical power source includes pulleys 17 and 17a, a belt 18, a power transmission shaft 19, and a shaft housing unit 20. Other power transmission designs, such as direct or gear driven units, may alternatively be used.

A differential pressure transducer 21 with a demodulator 22 monitors white water elution volume. This is the amount of white water drained from the furnish through the paper forming surface 12. The drainage level as a function of time is recorded by the computer. The drainage in this time period is referred to as the pulsation/gravity drainage.

When the white water elution reaches a predetermined level, a valve 23 opens and the vent valve 11 closes. Vacuum pressure cuts in to assist drainage. Another differential transducer 24 records the vacuum pressure developed in the vacuum monitoring chamber 3. The ultimate vacuum pressure that the vacuum monitoring chamber 3 can reach is adjustable by the size of the opening in the vacuum regulator 25, the capacity of the vacuum reservoir 26, and the pumping rate of the vacuum pump 27. The on/off positions of the valve 23 and the vent valve 11 can be controlled by the computer. As such, either a stepwise or a gradual increase in vacuum suction forces can be programmed for the vacuum drainage process, as desired.

When free white water drainage nears its end, air is drawn through the wet pad resulting in a pressure drop. This point is referred to as the wetline. Drainage in this period is referred to as the vacuum drainage. It represents the drainage rate accounted for on a paper machine on the first vacuum suction box until the wetline is achieved.

After the wetline is reached, the device can operate in two modes. The first is to cut off vacuum within a predetermined time period. The other mode allows the vacuum pressure to reach equilibrium. The former simulates the action of vacuum drainage elements on a paper machine, and its objective is to assess the wet pad consistency after the couch roll. The couch roll is the last vacuum suction unit on a paper machine. The latter allows for the evaluation of the wet sheet resistivity, which correlates to the formation of the paper sheet as it is formed in the device.

At the end of testing, the clamp means 28 which securely seals the middle chamber 2 and the vacuum monitoring chamber 3 during testing, can be opened manually and the wet pad removed for subsequent pressing and drying studies. White water can be sampled through a drain tube 29 for fines retention analysis.

A unique feature of this device is the capability to generate pulsation forces by a moving hydrofoil underneath the paper forming surface. Pulsation frequency is adjusted by modifying the speed of the motor 15. Amplitude and duration of pulsation depend on the design of the hydrofoil.

Any rigid object in close proximity, or in contact with a paper forming surface and moving in relation to this surface will generate hydrodynamic forces acting on the pulp. On a paper machine, the object (usually called a hydrofoil) is stationary and the paper forming surface sweeps over it. In the device of this invention, the object is rotating and the paper forming surface is stationary. When the hydrofoil is approaching, positive hydraulic pressure is exerted on a specific area in the furnish that remains above the paper forming surface. As the hydrofoil leaves a negative pressure (suction force) is generated. Therefore, pulsation can be created by sweeping the wire screen repeatedly with a hydrofoil. Such an effect can be achieved by objects of various kinds of shapes and designs, and by objects of various styles of movement.

Figure 2:
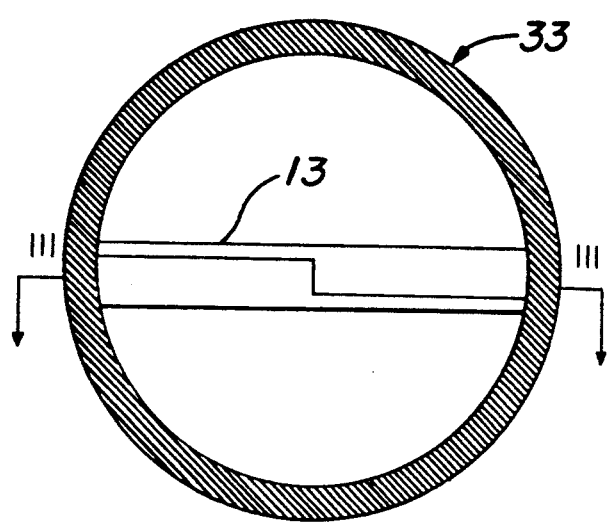
FIG. 2 is the top plan view of the hydrofoil assembly.
Figure 2A:
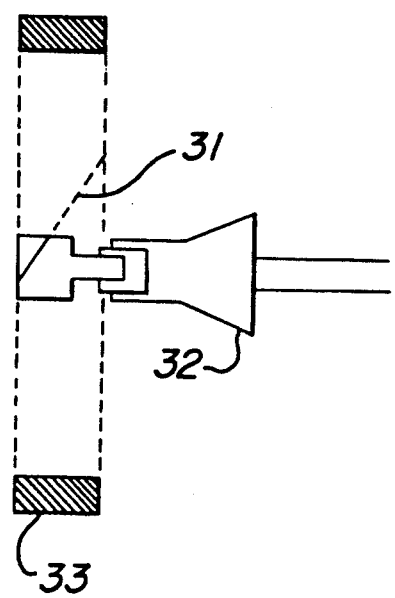
FIG. 2A shows the angle of divergence of the hydrofoil of FIG. 2.
Figure 3:
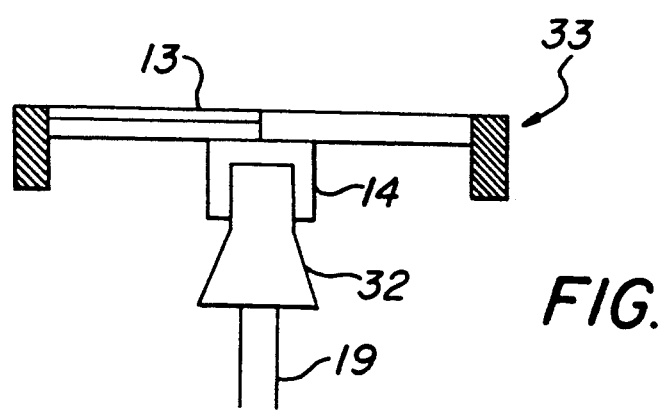
FIG. 3 is a cross section view of the hydrofoil assembly along line III of FIG. 2.

In a preferred embodiment, shown in FIGS. 2 through 3, the length of the hydrofoil blade 13 is substantially identical to the diameter of the sheet forming area. Upon rotation, the linear velocity (or pulsing force) is greater at the edge than near the center. When the blade is sweeping underneath the surface, the hydraulic force acting on the edges of the forming area will be high in amplitude but short in duration. On the other hand, the action near the center will be low in amplitude but long in duration. The momentum at any point on the forming area, calculated as the force times the duration, will therefore be the same due to the inverse relationship of these two dynamic factors.

The blade 13 in the preferred embodiment has a flat land and an 8-degree angle of divergence 31. Other shapes, landing distances, or angles will produce pulsation forces as well, although the frequency, the amplitude, and the duration may be different. The blade 13 sits on a holder 14 which is secured to a driver 32. A ring 33 around the blade 13 serves as a guide rail. Optionally, the holder 14 can be connected to the ring 33, which rotates inside a low friction bearing. This option can be used to enhance rotational stability. Another option is to have the blade 13 separated from the ring 33 and rotate freely. The blade is able to rotate in a range of 0–3000 rpm, limited by the maximum motor speed. For higher frequency pulsation, the hydrofoil unit can be made to have more than two blades. Symmetrical design is preferred.

It should be noted that the apparatus of this invention generates pulsation forces in a way somewhat different from the common practice of hydrofoils on paper machines. The paper forming surface on a paper machine is moving while the hydrofoils are stationary. Such a design is appropriate in a continuous process of papermaking, but is not suitable for a small size, batch process papermaking or testing apparatus. The unique feature of the apparatus of this invention is that it uses rigid and moving means to generate pulses while the paper forming surface is kept stationary. By doing so, this invention overcomes the technical problem of generating pulsation forces on a laboratory-sized, batch-process paper making or testing device.

Figure 4:
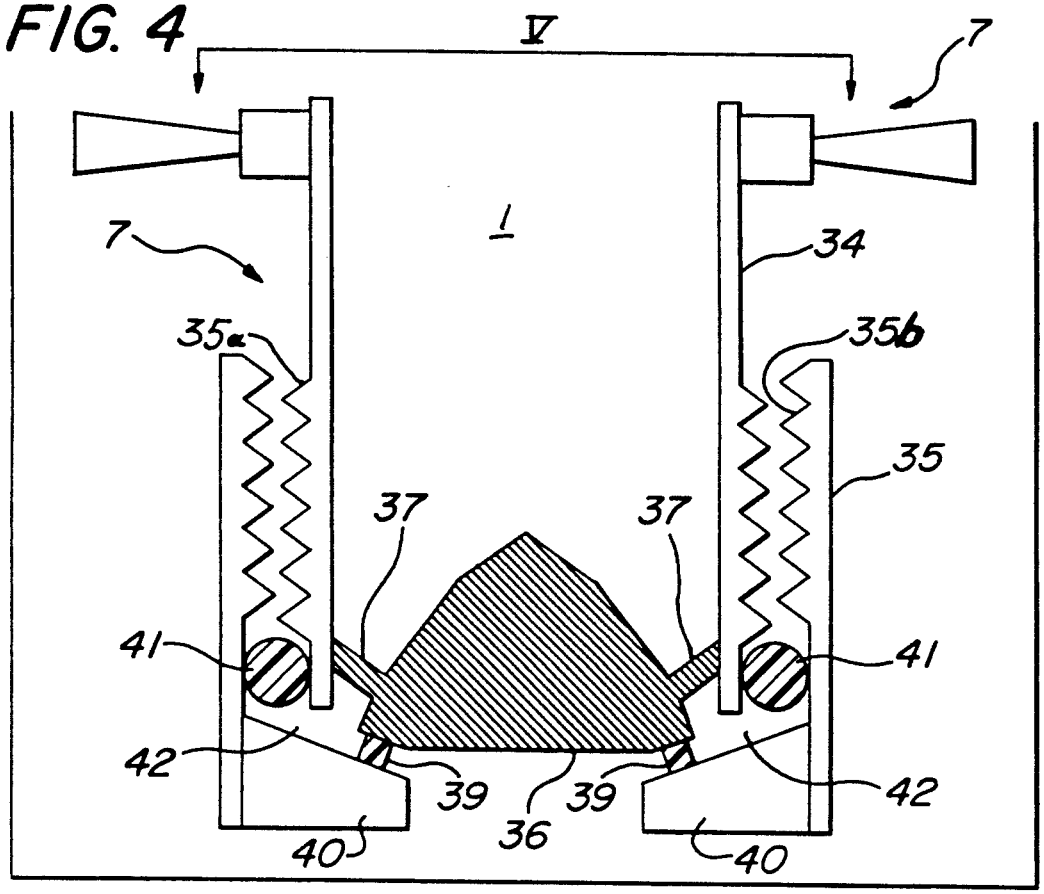
FIG. 4 is a cross section view of the pivoting valve.

Another unique feature of this device pertains to the method of furnish delivery. The device uses a furnish delivery valve, as detailed in FIG. 4, to direct the furnish onto the paper forming surface in a reproducible manner.

Figure 4A:
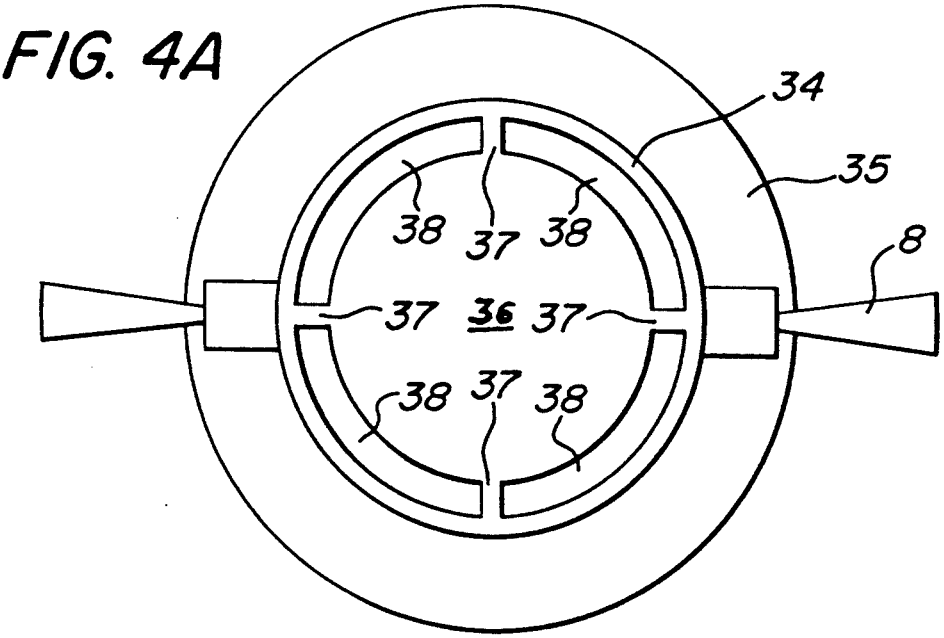
FIG. 4A is a top plan view along line V of FIG. 4.

The furnish delivery valve consists of an inner cylinder 34 having a screw thread 35a which is threadably engaged with a cooperating outer socket 35 having screw thread 35b. At the bottom of the inner cylinder is a flow distributor 36 having a substantially cone-shaped structure projecting upward into the upper chamber 1. The flow distributor 36 is bridged to the wall of the cylinder 34 by a plurality of connectors 37. Circumferentially disposed around the edges of flow distributor 36 are multiple drain slots 38 defined by the spaces between each of the plurality of connectors 37, as shown in FIG. 4A. The cone-shaped structure is designed to smooth out uneven angular velocity of flow created by the mixer, because stirring is not necessarily concentric. The drain slots 38 are closed by a seal 39 acting against a rim 40 at the bottom of the outer socket 35. A ring shaped seal 41 seals the gap between the inner cylinder 34 and the outer socket 35. The handle 8 is securely fixed to the outer surface of the inner cylinder 34. The handle 8 is used to turn the inner cylinder 34 about screw thread 35b causing inner cylinder 34 to rise vertically, and open the drain slots 38. Furnish swirls and drops through the slots 38 into a flow channel 42 which directs the furnish toward the center of the chamber 2. The valve 7 is designed to optimize the centrifugal force, preventing the furnish from being sprayed toward the wall of the middle chamber 2. Instead, it will spread substantially evenly over the paper forming surface 12.

A vent valve delay mechanism generating backup pressure is used to control the force of impingement. The impingement control system includes the switch 9 and the vent valve 11. The system is operated by computer 10. The vent valve is closed initially. When the valve 7 is turned to the open position, the handle 8 hits the switch 9 and triggers the computer 10 to start timing the vent valve delay mechanism. Meanwhile, furnish drops down to the middle chamber 2. A sufficient amount of backup pressure is generated within the bottom chamber 3 without the assistance of external air supplies. The backup pressure allows the furnish to form a pool on the paper forming surface 12 to a height depending on the predetermined vent valve delay time. Once the time expires, the vent is opened and drainage begins. To sufficiently attenuate the impingement force of 1000 cc furnish, a vent valve delay time in the range of 0–3 seconds is suggested.

Figure 5:
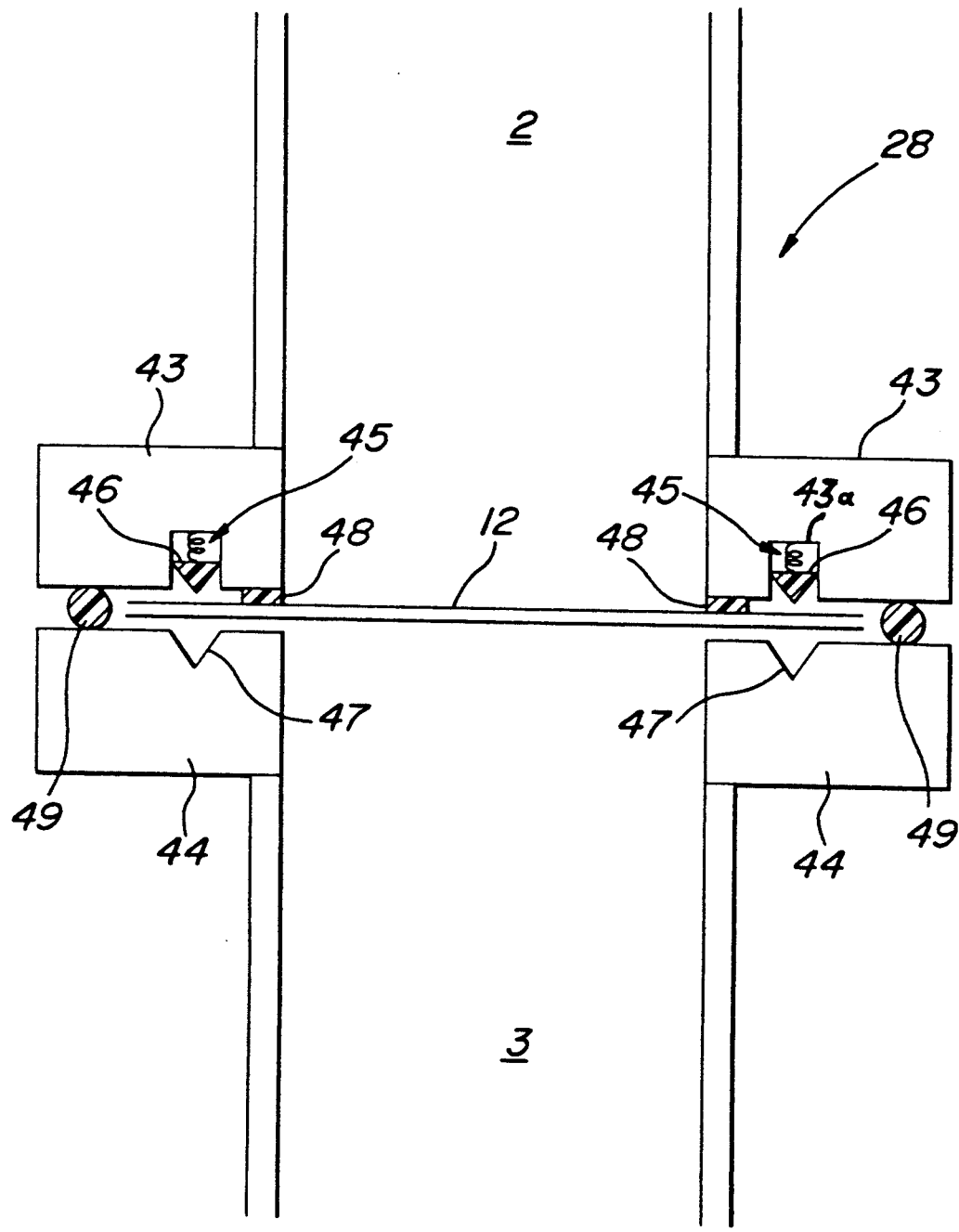
FIG. 5 shows a cross section view of a preferred paper forming surface tensioning assembly.

The apparatus of this invention uses interchangeable paper forming surface materials. Therefore, it can test the dewatering efficacy of anything from forming fabric to varying mesh sizes of screens. FIG. 5 shows a paper forming surface tensioning assembly. The paper forming surface 12 is secured between a first casement 43, defining the middle chamber 2, and a second casement 44, defining the bottom chamber 3. A groove 43a is circumferentially disposed in the bottom surface of casement 43. It contains a plurality of tension springs 45 which urge a ring 46 to engage the paper forming surface 12 and seat it securely with tension into an opposing circumferential trough 47 on the top surface of the second casement 44. A ring-like seal 48 located radially inward from the circumferential trough 47 prevents furnish from leaking out from the edges of the forming area. Another ring-like seal 49 located radially outward from the circumferential trough 47 helps maintain vacuum pressure. Other options for tensioning the paper forming surface may be acceptable as long as they secure the paper forming surface, seal the vacuum, and prevent the furnish slurry from leaking.

Figure 6:
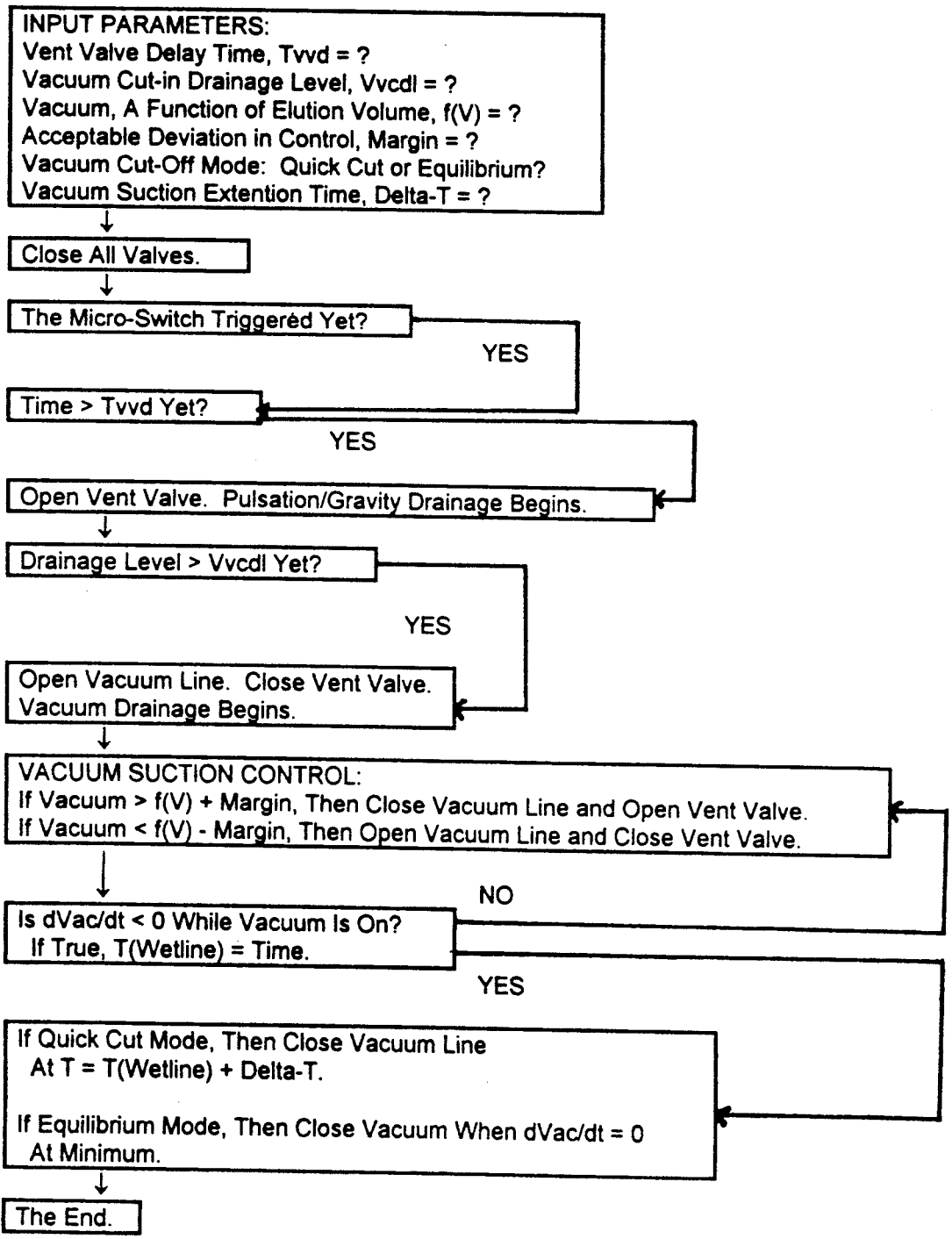
FIG. 6 is a flow chart representing the process steps controlled and recorded by the computer.

The apparatus of this invention employs a computer to sequentially control the various steps in which high speed computations are necessary. Control parameters must be entered into the computer before testing. FIG. 6 represents a flow chart of the control program.

The computer controls the vent valve delay time. By doing so it attenuates the impingement forces of a furnish slurry on the wire screen. A control parameter is the vent valve delay time (Tvvd), which is set in the range of 0–3 seconds. The vent valve 11 is set to be closed initially, allowing backup pressure to build up when the furnish slurry drops down onto the paper forming surface 12. When valve 7 is opened manually, the handle 8 triggers the microswitch 9. The computer 10 starts timing, and it will command the vent valve 11 to open when vent valve delay time expires.

The computer 10 initiates vacuum suction after pulsation/gravity drainage reaches a predetermined elution level (Vvcdl). The Vvcdl is set preferably in the range of 50–95% of the initial furnish volume. Or, if desired, it can be set at a lower level to study the effect of matrix sealing due to vacuum suctions. During vacuum drainage, the vacuum pressure is regulated such that it increases either stepwise or gradually in simulating vacuum boxes of various kinds. Precise control can be achieved by switching on/off the vacuum line solenoid valve and the vent valve. The desired vacuum pressure is assigned as a function of drainage level f(V). A small deviation in vacuum pressure, denoted as the "margin" in FIG. 6, is allowed. If the actual vacuum pressure is less than the desired value minus the margin, the solenoid valve will open and the vent valve closes. Reverse actions will be taken if the actual vacuum pressure is higher than the desired value plus the margin. The smaller the margin, the more precise is the control. However, it is limited by the response speeds of the valves. A margin in the range of 0.02–0.5 inch-Hg is found appropriate for getting reproducible results.

The computer also determines the wetline. Herein, wetline is defined as the point where air starts to penetrate the wet pad. The computer recognizes the wetline by mathematical computation as follows. At wetline, the vacuum pressure is a maximum (or the end of a plateau) but starts to drop even if the vacuum line is on. The first order derivative of vacuum pressure, dvac/dt, is zero on the plateau, but it becomes negative at and after the wetline. After the wetline is reached, the computer commands the vacuum system to shut off within a period of time depending on the mode of operation. Two such modes, referred to as Quick Cut and Equilibrium, may be applied as desired. In the Quick Cut mode, the vacuum will be shut off within a short time after wetline. The extension time is denoted as "delta-T" in FIG. 6. The objective of such an operation is to assess the wet pad consistency after couch. When delta-T is between 0.01–5 seconds, the wet pad consistency is normally in the range of 15%–20%. In the Equilibrium mode, the vacuum suction continues until a pressure equilibrium is reached. The purpose is to evaluate the porosity of the wet pad.

The apparatus and method of this invention can be used to evaluate drainage, retention, and formation in one test. Assessment of these variables covers the entire range of free water drainage. Retention data is obtained from gravimetric analysis of the fines in the white water. Wet pad consistency and dry sheet weight are measured for the pad as it is formed from the drainage studies. Drainage data are acquired by the computer. They are the white water drainage and the vacuum pressure curves. The pulsation/gravity drainage, the vacuum drainage, the wetline, the dryline, and the equilibrium vacuum pressure are major dependent variables evaluated from the two curves. The control system of the device has the capability to set parameters to mimic the free water removal process on most paper machines via level control and duration of the pertinent variables. The drainage rate at any specific stage of the dewatering process can be determined, because the entire process is recorded. When coupled with retention data, the equilibrium drainage properties can be determined.

To setup a drainage experiment, the vacuum pump must be first turned on and the vacuum pressure in the reservoir must reach and stay at a predetermined level. The vacuum regulator must be adjusted to balance the system. For convenient operation, the reservoir has a vacuum pressure of 14 inch-Hg, which after dilution by volume will be able to provide a plateau suction pressure of 8–13 inch-Hg, depending on the volume of furnish. The paper forming surface is placed on top of lower casement, and then clamped tightly against the upper casement. The sheet forming area is circular and is approximately 4 inches in diameter. The preferred paper forming surface is a wire screen (about 100-mesh). However, other mesh sizes can be used. The rotational speed of the hydrofoil blade is in the range of 300–3000 rpm depending on the paper machine speed and the types of furnish to be simulated.

The furnish to be tested is poured into the upper chamber and stirred with a mixer at approximately 1400 rpm. Other speeds may be used to study shear sensitivity of drainage or retention aids. The furnish volume may be in the range of 300 to 1200 cc. Consistency is in the range of 0.05 to 0.5% depending on the basis weight. For drainage efficacy tests a constant volume of 1000 cc is used as a convenient standard. Wet end additives are mixed into the furnish in this stage.

To start drainage, valve 7 is opened manually, allowing the pulp furnish to drop to the middle chamber 2. The handle 8 signals the computer to start the vent valve delay process. All processes after computer 10 is activated are under automatic control. The control program is depicted by the flow chart in FIG. 6. Delay of venting is in the range of 0–3 seconds. A delay of 1.5 seconds is considered optimal. During this time, the bottom chamber 3 is air-tight, causing a backup pressure to act against the impingement force of the furnish. Furnish slurry forms a pool on the top of the paper forming surface to a volume level depending on the time length of delay.

As soon as the vent valve opens, white water starts to drain through the paper forming surface due to gravity and hydrofoil pulsation forces. A differential pressure transducer measures the height of water column collected in the bottom chamber. When drainage reaches a predetermined level, usually set at 50–95% of the total furnish volume, the computer commands the vent valve to close and the vacuum-line solenoid valve to open. A vacuum is now produced in the bottom chamber to assist the drainage of the pulp slurry. A pressure transducer measures the vacuum pressure, which rises according to the vacuum control program. The vacuum line is allowed to open fully when vacuum drainage nears its end, simulating the action of a high vacuum box on a paper machine. At this point, the vacuum pressure rises to a plateau value depending on the furnish size, the vacuum histogram, and on how fast the wetline is approaching.

While the vacuum pressure rises in the bottom chamber, the computer analyzes the vacuum data. It controls the vacuum pressure depending on the assignment of vacuum control function, f(V). If the actual vacuum pressure is greater than f(V) plus a margin, the vent valve will open and the vacuum solenoid valve will close to release the vacuum slightly. If the actual vacuum pressure is too low, a reverse action will be taken to increase the vacuum pressure.

The computer will recognize the first drop in vacuum pressure (while the vacuum line is on), which takes place when air starts to break in through the wet mat. This point, referred to as the "wetline", is used by the computer as a parameter for further process control. After the wetline, the device continues to monitor and control the vacuum pressure in two modes. The first mode is to cut off the vacuum pressure within a short time period, simulating the definite distance of the paper forming surface travelling over the vacuum drainage elements on whatever paper machine is being simulated. The holding period is in the range of 0.01 second–5 seconds. Once the vacuum is cut off, the wet pad should be removed immediately from the paper forming surface and then weighed. Wet pad consistency can be determined by conventional gravimetric methods. This value reflects the on-machine wet pad consistency after the couch roll.

The second mode allows the vacuum to continue until reaching equilibrium. The equilibrium vacuum pressure is used to determine the porosity of the wet pad, which reflects the formation of the wet pad. Wet pad consistency after vacuum equilibrium can be utilized for additional information. Although the results tend to be higher than the true couch consistency, the trend of the two values is usually very similar.

After free water drainage is over, the white water can be sampled and fines consistency determined by gravimetric analysis. Fines retention data from this invention substantially simulate the value observed on paper machines. The wet pad made using said process can be used for subsequent pressing, drying, or ashing studies.

EXAMPLES AND DATA

EXAMPLE 1

Data Curves and Reproducibility Studies

The furnish tested was a mixture of Old Corrugated Containers and Old Newsprint at a respective ratio of 85:15. A furnish volume of 1000+2 cc, having a consistency of 0.132+0.002% was used for each test. The furnish has a fines constant of 27.88+0.02%. Hydrofoil blade speed was set at 500 rpm. The vacuum system was set to cut in when pulsation/gravity drainage reached a level of 700 cc. The vacuum reservoir was set to have 14 inch-Hg. A one-step vacuum suction control program was used in this example. Mixer speed was set at 1400 rpm. Vent valve delay was 1.5 seconds. A wire screen of 100 mesh was used.

A conventional high molecular weight cationic polyacryl amide copolymer was added and allowed to mix with the furnish for 15 seconds. The pivoting valve was then opened to deliver the furnish and activate the impingement control. After a delay of 1.5 seconds the vent valve opened and the white water started draining through the paper forming surface. Two pressure transducers recorded the drainage level and the vacuum pressure, and the vacuum pressure, respectively. When white water reached the 700 cc level, the solenoid valve opened and the vent valve closed. Vacuum pressure in the bottom chamber rose immediately to a plateau about 12-13 inch-Hg and stayed at that level for a short time, then dropped as soon as the wetline was reached. The vacuum was allowed to continue to reach an equilibrium.

At the end of drainage testing, the wet pad was weighed and then dried at 120° C. in an oven for dry sheet weight and couch consistency evaluation. White water was filtered to determine the fines retention.

Table 1 shows the reproducibility of the percent of fines retention (% FR), the wet pad consistency after couch (% Cch), dry sheet weight in grams (Wtdry), the pulsation/gravity drainage time in seconds (TV700), the vacuum drainage time in seconds (Towet), and the air-flow resistance in units of inch-Hg minute per liter (RIndx). Note that the fines content (Fww) in white water is determined by the gravimetric method. The resistance is determined from the equilibrium vacuum pressure. The pulsation/gravity drainage, denoted as TV700 in this example, is defined as the time for white water to reach the 700 cc level. The vacuum drainage time, Towet, is the period from the vacuum cut in to the wetline.

TABLE 1

Drainage Reproducibility

| Replica No. | % FR | % Cch | Wt dry | TV700 | Towet | Rindx | Fww |
|---|---|---|---|---|---|---|---|
| #1 | 88.19 | 17.39 | 1.306 | 31.52 | 2.97 | 0.140 | 0.044 |
| #2 | 88.48 | 17.26 | 1.283 | 32.02 | 3.30 | 0.141 | 0.042 |
| #3 | 88.67 | 17.38 | 1.283 | 34.00 | 3.14 | 0.141 | 0.042 |
| #4 | 88.09 | 17.47 | 1.244 | 32.85 | 3.14 | 0.137 | 0.043 |
| #5 | 89.30 | 16.86 | 1.283 | 31.03 | 3.24 | 0.141 | 0.039 |
| avg | 88.54 | 17.27 | 1.2798 | 32.284 | 3.158 | 0.14 | 0.042 |
| st. dev | 0.429 | 0.216 | 0.0199 | 1.0479 | 0.1121 | 0.001 | 0.0017 |
| % dev | 0.485 | 1.254 | 1.5622 | 3.2460 | 3.5510 | 1.106 | 3.984 |

Figure 9:
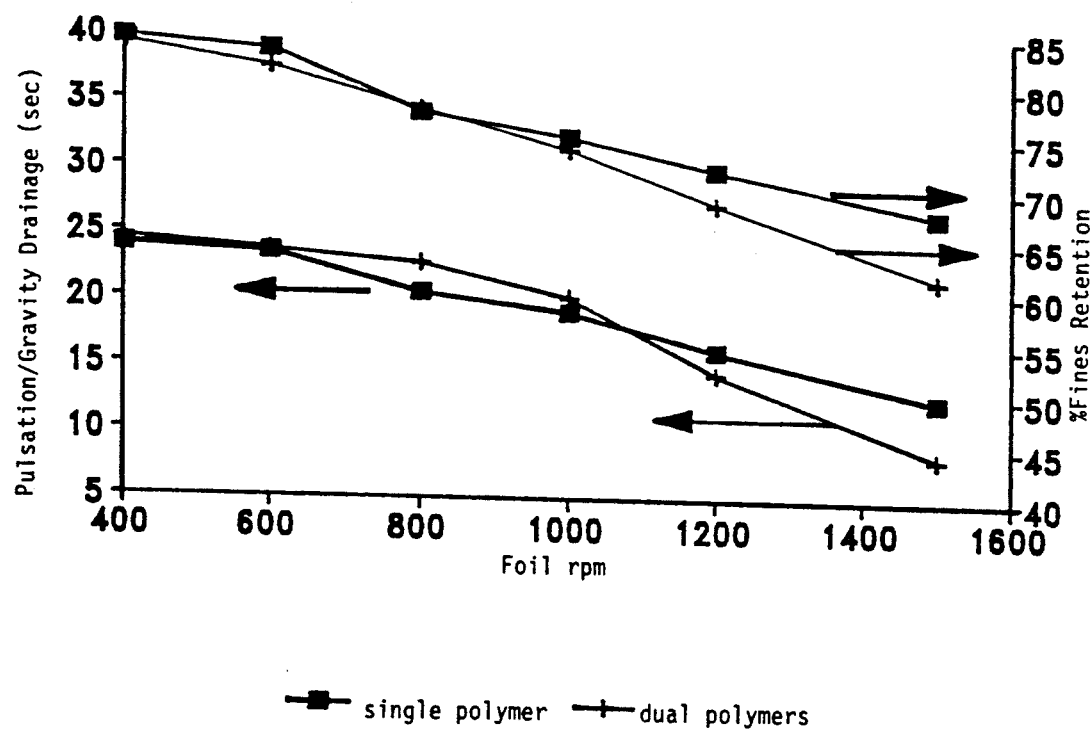
FIG. 9 shows pulsation/gravity drainage time and fines retention.

The results indicate that the margin of error involved in this testing method is very small because a much greater deviation can be found between furnishes treated with various kinds of polymers. Examples to support this point are shown in FIG. 9, which will be discussed later. Therefore, the device can be used comfortably to compare performances of drainage or retention aids.

Figure 7:
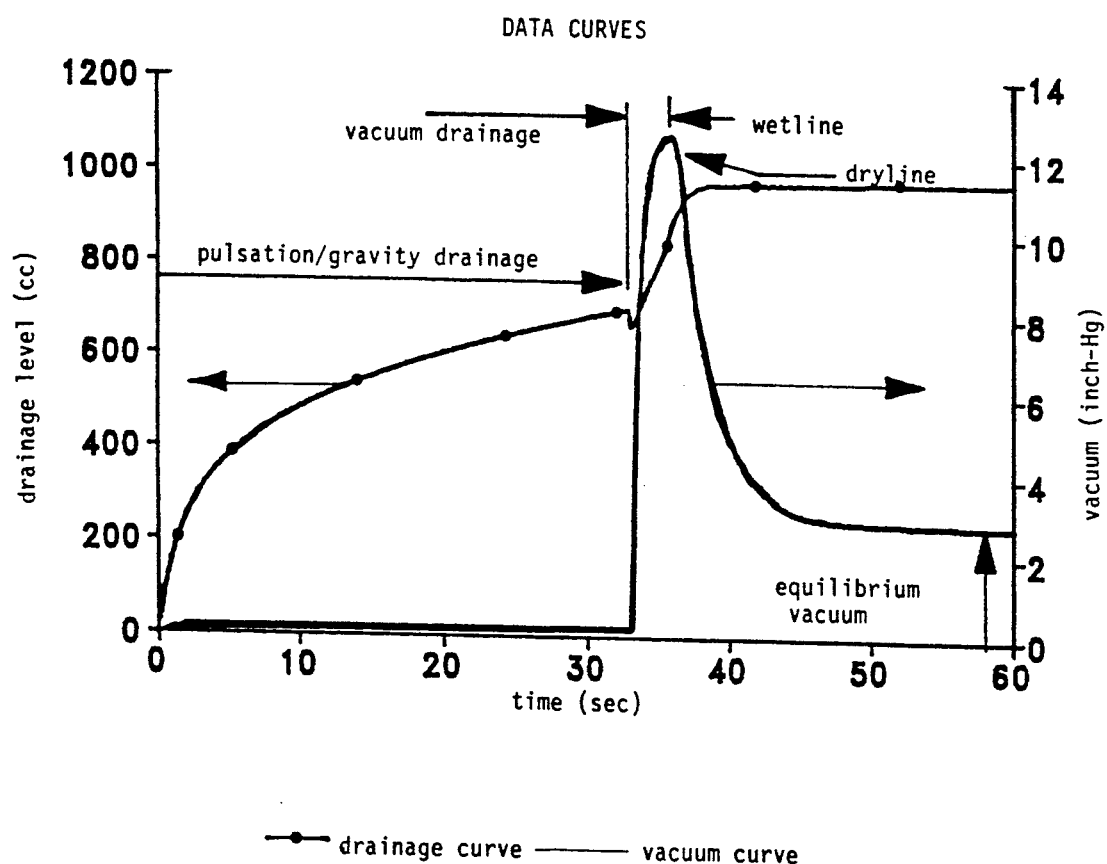
FIG. 7 shows the data generated from Example 1.

FIG. 7 demonstrates the data curves obtained from one of the replica tests of Table 1. Two curves, namely the white water drainage curve and the vacuum curve, were obtained. The drainage curve represents the accumulative white water elution volume as a function of time. The curve rises sharply at the beginning, but then levels off gradually, indicating that the pulsation/gravity drainage was more difficult as the furnish consistency increased. At this time, there was no hydrostatic vacuum in the bottom chamber and therefore the vacuum curve is flat. (Note: The pressure transducer measures the hydrostatic vacuum only. It does not reflect the hydro-dynamic vacuum forces generated by the rotating hydrofoils). When white water drainage reached the 700 cc level, the vacuum cut in and the vacuum pressure rose sharply to reach a plateau, as shown by the curve. The point showing the first "drop" in vacuum after it reached the plateau is the wetline. At the wetline, air starts to break in but residual water may reseal the pores due to a surface tension effect. There is another deflection point, believed to be the dryline, located closely after the wetline. The slope of the vacuum curve at this point is the sharpest, i.e., maximum (in absolute value) of the first order derivatives. Maximal slope suggests that air breaks in at the highest rate, because free water had been drained completely and the resealing effect stopped at the dryline. This example demonstrates the equilibrium mode, in which the vacuum was allowed to continue until reaching an equilibrium. Since air continued to flow in, the vacuum pressure dropped gradually and eventually reached an equilibrium. The equilibrium vacuum pressure reflects the balance between the intake rate of air and the pumping rate of the vacuum pump. It determines the resistivity (or inversely, the porosity) of the wet pad.

EXAMPLE 2

Reproducibility in Control for Gradually Increasing Vacuum Suctions

Alkaline Fine Paper furnish (SW:HW=50:50, 15% TiO2, pH=7.5) was used in this example. Foil blade speed was set at 800 rpm. A volume of 1000+2 cc furnish, consistency 0.130+0.002%, without treatments was used in replica tests. Vacuum control was set to cut in when the drainage level reached 700 cc. Then, the vacuum pressure was programmed to rise linearly to 6 inch-Hg when the drainage level reached 900 cc. Then, maximal 12 inch-Hg vacuum pressure will cut in to assist drainage till the end. Margin of control was set allowing for 0.5 inch-Hg deviation.

Figure 8:
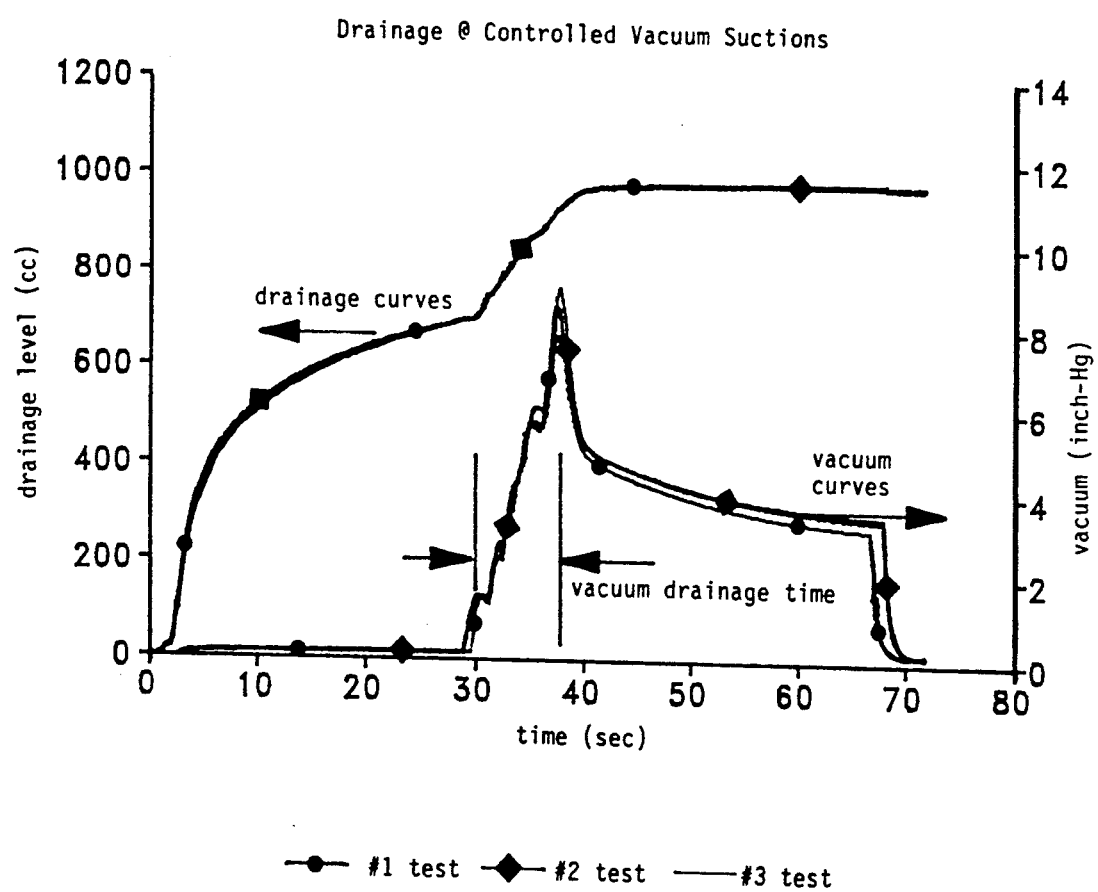
FIG. 8 shows drainage values from Example 2.

The actual vacuum curves obtained are shown in FIG. 8. As compared to the one-step vacuum curves shown in other examples, FIG. 8 shows vacuum curves rising more slowly over the vacuum drainage period. It can be seen that the actual vacuum pressures follow the instruction of the control program very well in the drainage range of 700 cc to 900 cc. After the 900 cc level, the actual vacuum pressure reaches a plateau of about 8-10 inch-Hg at wetline, although a maximum of 12 inch-Hg vacuum suction force was applied. This is due to the fast approaching wetline and the drawing in of air. Clearly shown in FIG. 8, the vacuum drainage time is reproducible. Among the replica tests, the vacuum curve #2 almost overlaps with curve #3. The drainage curves have a very small variance.

EXAMPLE 3

The Effect of Pulsation Forces on the Drainage and Retention Performances of Polymers A unique feature of the apparatus of this invention is the capability to generate pulsation forces from underneath the paper forming surfaces. Example 3 demonstrates the effect of the hydrofoil. The furnish was Light Weight Coated, 1000+0.002 cc, 0.066% consistency. The hydrofoil blade rpm is variable. The pulsation/gravity drainage is assessed up to 600 cc, and then one-step vacuum cuts in. Vent valve delay was 1.5 seconds. The reservoir vacuum was 14 inch-Hg.

The retention/drainage programs were compared to demonstrate that retention and drainage performances can be affected by the pulsation forces. The first polymer program used a high molecular weight cationic polyacrylamide copolymer, denoted as the "single polymer" in FIG. 9. The polymer was added to the furnish and mixed for 15 seconds before testing. The second program is a dual system. A low molecular weight, high charge density cationic polymer was added to the furnish and mixed for 15 seconds, followed by adding and mixing for 15 more seconds a high molecular weight anionic polyacrylamide before the furnish was dropped. Other subsequent procedures were the same as in Example 1 except the pulsation/gravity drainage was assessed at a lower level.

The pulsation/gravity drainage time and the percent fines retention are shown in FIG. 9. It can be seen that fines retentions of both programs drop, and drainage times decrease a hydrofoil rpm is increased. Therefore, the apparatus of this invention proves its capability of being able to reveal the effects of turbulence, i.e., that both retention and drainage time decrease as the turbulence forces increases. Furthermore, the device shows that polymer performance ranking changes as hydrofoil speed increases. When hydrofoil speed is less than 1000 rpm, both drainage and retention are better in the single polymer treated system than the dual polymer system. At a speed of 1200 rpm or higher, the retention in the former program is still higher when compared to the dual program. However, the trend in the drainage rate is reversed. This example clearly demonstrates that the device of this invention can be used to evaluate the performance of a drainage aid which may depend on the extent of turbulence, or equivalently, machine speed.

EXAMPLE 4

Effect of Furnish Impingement

Groundwood furnish refined to 125 CSF was used in the study. Each of the three tests shown in FIG. 8 used 1000 cc, 0.07% consistency, of furnish. Hydrofoil speed was 1200 rpm. Vacuum cut in at 700 cc. In these studies, the vent valve delay time was a variable, in the range of 0-2 seconds.

Furnish was treated with a high molecular weight cationic polyacrylamide copolymer at a dosage rate of 1.25#/T, followed by 15 seconds of mixing. The furnish delivery valve was then opened. All other subsequent procedures are the same as in Example 1.

Figure 10:
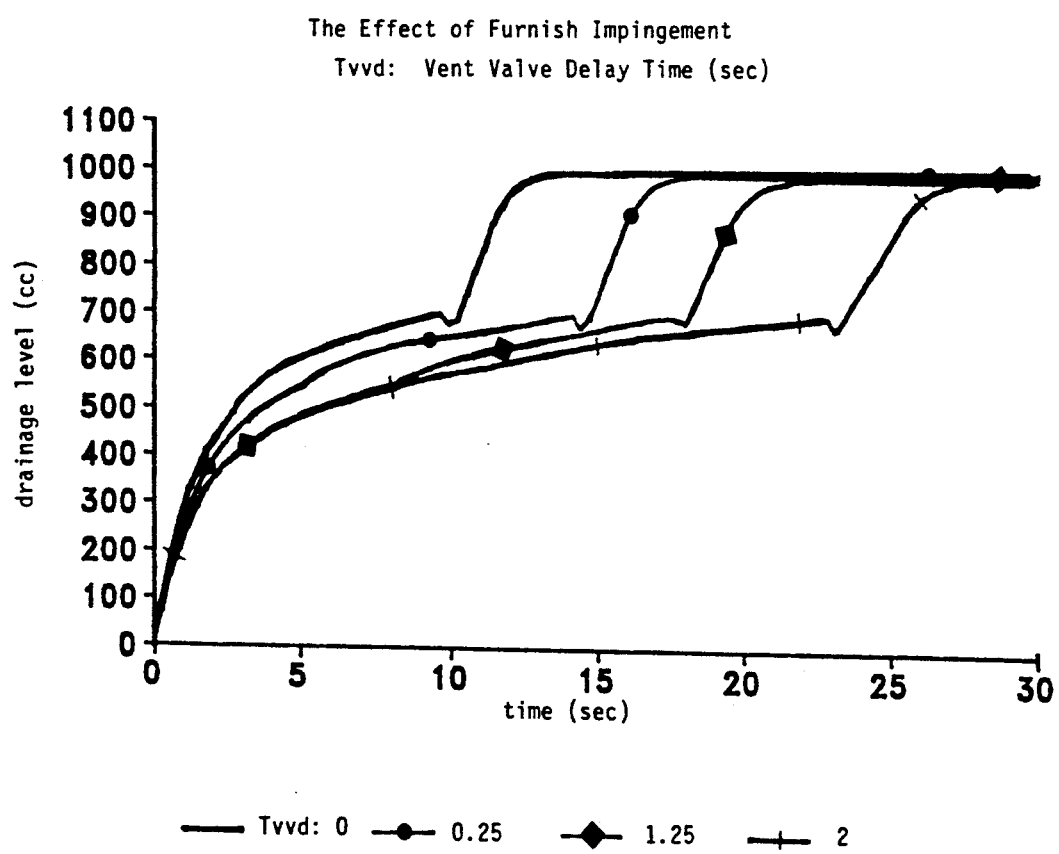
FIG. 10 shows the effects of varying impingement forces.

As shown in FIG. 10, the drainage curve with zero vent valve delay (Tvvd=0) rises very sharply at the very beginning due to a high impingement force. High impingement causes significant loss of fines and poor formation. With 0.25 second vent valve delay time, the furnish can distribute itself more evenly on the screen. Retention and formation are better, although the first pass drainage is slower as compared to the zero delay system. These data indicate that longer vent valve delay times result in slower drainage rates.

EXAMPLE 5

Wet Pad Resistivity vs. Dosage

Wet pad resistivity can be determined from the equilibrium vacuum pressure. Resistivity can be used as an index to compare the formation of sheets, unless the sheets contain substantially different amounts of fines or basis weight. Higher resistivity suggests better formation.

Table 2 shows the resistivity of wet pads obtained from a furnish treated with various polymers. Procedures of testing were the same as in Example 1, except the furnish was Old Corrugated Container with a consistency of 0.2%.

Three dosages were tested for each polymer. In high molecular weight cationic polymer treated systems, the wet pad resistivity dropped as the dosage increased. The trend suggests that high molecular weight cationic polymers tend to hurt formation when using high dosage. In this case, resistivity is dominated by formation. With low molecular weight cationic polymers, resistivity increased as the dosage increased, because these polymers are not flocculants but they are coagulants which improve formation.

TABLE 2

| Polymer | Resistivity and Dosage | | |
|---|---|---|---|
| | #/T | % FR | Resistivity |
| Blank | 0 | 60.5 | 0.156 |
| Polymer I | 0.5 | 71.36 | 0.144 |
| Polymer I | 0.85 | 78.38 | 0.137 |
| Polymer I | 1.25 | 80.29 | 0.131 |
| Polymer II | 0.5 | 75.2 | 0.137 |
| Polymer II | 0.85 | 75.42 | 0.128 |
| Polymer II | 1.25 | 78.23 | 0.121 |
| Polymer III | 1 | 62.93 | 0.157 |
| Polymer III | 2 | 66.29 | 0.16 |
| Polymer III | 3 | 66.95 | 0.165 |
| Polymer IV | 1 | 62.59 | 0.157 |
| Polymer IV | 2 | 63.88 | 0.18 |
| Polymer IV | 3 | 66.12 | 0.196 |

Polymer I: high molecular weight, low charge density cationic polyacrylamide polymer.
Polymer II: high molecular weight, low charge density cationic polyacrylamide polymer.
Polymer III: low molecular weight, medium charge density polyamidoamine.
Polymer IV: low molecular weight, high charge density polyamine.

What we claim is:

1. An apparatus to evaluate the drainage, retention and formation characteristics of a paper pulp furnish during the formation of a paper sheet comprising:

a furnish delivery chamber disposed above a paper sheet forming chamber and a white water collection and vacuum chamber, a furnish delivery valve disposed between the furnish delivery chamber and the paper sheet forming chamber consisting of a cone-shaped flow distributor, a stationary paper forming surface disposed between the paper sheet forming chamber and white water collection and vacuum chamber, a rotatable blade said blade being substantially the same size as the paper forming surface disposed in the white water collection and vacuum chamber underneath and in close proximity to the paper forming surface to generate a pulsation force consisting of alternating positive hydraulic pressure and negative suction pressure on the furnish above the paper forming surface, means for measuring the white water collected in the white water collection and vacuum chamber, means for measuring the pressure in the white water collection and vacuum chamber, means for determining drainage and formation characteristics from said measured values of the white water collected and the pressure, and means for sampling the white water for fines retention analysis.

2. The apparatus of claim 1 wherein the blade is connected by a power transmission shaft to a mechanical power source.

3. The apparatus of claim 2 wherein the mechanical power source provides the energy necessary to rotate the blade.

4. The apparatus of claim 1 wherein the paper forming surface is a forming fabric.

5. The apparatus of claim 1 wherein the paper forming surface is a screen.

* * * * *